United States Patent [19] [11] 4,332,735
Alaimo et al. [45] Jun. 1, 1982

[54] ANTIFUNGAL COMPOUND

[75] Inventors: Robert J. Alaimo; Joseph E. Gray; George M. Klein, all of Norwich, N.Y.

[73] Assignee: Morton-Norwich Products, Inc., Norwich, N.Y.

[21] Appl. No.: 281,236

[22] Filed: Jul. 6, 1981

[51] Int. Cl.$^3$ ............................................ C07D 307/46
[52] U.S. Cl. ..................................... 549/496; 424/285
[58] Field of Search ....................................... 260/347.3

[56] References Cited

U.S. PATENT DOCUMENTS 3,217,037 11/1965 Payne et al. ......................... 564/255
3,957,867 5/1976 Bukowick ...................... 260/347.3 X

OTHER PUBLICATIONS

Saldabols et al., Chemical Abstracts, vol. 82, (1975), 72680n.

Primary Examiner—Richard Raymond
Attorney, Agent, or Firm—Anthony J. Franze

[57] ABSTRACT

The compound 5-[3,4-dimethoxyphenyl]-N-{[(methylamino)carbonyl]oxy}-α-oxo-2-furanethanimidoyl chloride is useful as an antifungal agent.

1 Claim, No Drawings

ANTIFUNGAL COMPOUND

This invention is concerned with the compound 5-[3,4-dimethoxyphenyl]-N-{[(methylamino)carbonyl]oxy}-α-oxo-2-furanethanimidoyl chloride. This compound possesses antifungal activity. In particular it is inimical to the growth of *Microsporum canis* in the commonly employed in vitro technique for determining antifungal activity at a concentration of about 250 mcg. of compound per milliliter of test media. Furthermore, it is also efficacious in the in vivo treatment of fungal infections. Thus, when administered per os as an aqueous suspension at a dose of about 35 mg/kg t.i.d. for five days post-infection to mice in which *Torulopsis glabrata* infection had been induced by the iv administration in physiologic saline of 2,000,000 cells of *T. glabrata*, a 40% reduction in viable yeast cells present in spleen and heart tissue was effected.

The compound of this invention can be readily combined in known carriers, adjuvants and vehicles to provide compositions adapted to control or eradicate fungal growth.

The presently preferred method for the preparation of the compound of this invention is here below set forth.

A. 5-(3,4-DIMETHOXYPHENYL)-2-FURYL METHYL KETONE

A mixture of 332 g (1.75 moles) of 4-aminoveratrole hydrochloride, 605 ml of concentrated hydrochloric acid and 230 ml of water was heated with steam for 20 minutes at 80° and then cooled to 0°. A solution of 121 g (1.75 moles) of sodium nitrate in 425 ml of water was added dropwise while maintaining the temperature between 0°–5° by means of an ice bath. The resulting mixture was kept below 5° for one hour. The pH was then adjusted to 3.5 by the addition of ca. 2500 ml of saturated sodium acetate solution. A solution of 193 g (1.75 moles) of 2-acetyl furan in 200 ml of acetonitrile was added followed by a solution of 35 g of $CuCl_2 \cdot 12 H_2O$ in 300 ml of water. The ice bath was removed and the reaction mixture was stirred at ambient temperature for 30 minutes. The mixture was stirred at room temperature overnight and extracted with 1×750 ml and 3×500 ml portion of ether. The ether extracts were combined and washed with 2500 ml of 6% sodium carbonate solution, with 3000 ml of water and dried over magnesium sulfate. The ether was removed on the Calab evaporator and the residual oil obtained was distilled under reduced pressure, yielding 75 g of oil, b.p. 180°–195° at 0.6 mm. The oil upon trituration with hexane solidified. The solid was filtered and air-dried to yield 71 g (17.4%). An analytical sample was obtained by recrystallizing a sample from hexane/Darco, m.p. 95°–97° C. (Mel-Temp).

Anal. Calc'd. for $C_{14}H_{14}O_4$: C, 68.28; H, 5.73. Found: C, 67.99; H, 5.68.

B. N-(HYDROXY)-[5-(3,4-DIMETHOXYPHENYL)-2-FURANYL]-α-OXOETHANIMIDOYL CHLORIDE

Nitrosyl chloride (25 g; 0.38 mol) was absorbed in carbon tetrachloride (488 ml) with ice bath cooling over a period of 12 minutes. A suspension of A. (37 g; 0.15 mol) in carbon tetrachloride (150 ml) was added in small portions over a period of 35 minutes.

The reaction mixture was warmed to 34° over a period of 20 minutes, and heated at 34°–40° for 1 hour (vigorous evolution of HCl). After cooling, the product was collected, washed with carbon tetrachloride, and air dried to give 34.9 g (75.0%) of small, orange-brown crystals. TLC on silica gel, solvent system chloroform-methanol (9:1), showed spots at $R_f$ 0.96 and 0.67 (impurity). After three recrystallizations from acetonitrile, the analysis was:

Calc'd. for $C_{14}H_{12}ClNO_5$: C, 54.30; H, 3.91; N, 4.52. Found: C, 54.84; H, 3.93; N, 4.96.

C. 5-[3,4-DIMETHOXYPHENYL]-N-{[(METHYLAMINO)CARBONYL]OXY}-α-OXO-2-FURANETHANIMIDOYL CHLORIDE

The N-Hydroxy compound, 17.5 g, was suspended in tetrahydrofuran (60 ml) and methyl isocyanate (11.8 ml) was added. Triethylamine (0.3 ml) was added over a period of 5 minutes at 10°. The mixture was heated at 45° for 20 hours, cooled, filtered, washed with ether and air dried to 15.0 g (73%). TLC (chloroform:methanol, 95:5) showed a trace of starting material. The analytical sample was obtained by recrystallization from acetonitrile (50 ml/g) and was dried at 60° in vacuo. Recrystallization of 11.2 g from acetonitrile gave 8.0 g; m.p. 194°–195°.

Anal. Calc'd. for $C_{16}H_{15}ClN_2O_6$: C, 52.40; H, 4.12; N, 7.64. Found: C, 52.82; H, 4.24; N, 7.83.

What is claimed is:

1. The compound 5-[3,4-dimethoxyphenyl]-N-{[(methylamino)carbonyl]oxy}-α-oxo-2-furanethanimidoyl chloride.

* * * * *